United States Patent
Liu et al.

(10) Patent No.: US 10,258,824 B2
(45) Date of Patent: Apr. 16, 2019

(54) METHODS AND DEVICES FOR RECORDING EXERCISE

(71) Applicant: Xiaomi Inc., Beijing (CN)

(72) Inventors: Huayijun Liu, Beijing (CN); Ke Wu, Beijing (CN); Tao Chen, Beijing (CN)

(73) Assignee: Xiaomi Inc., Beijing (CN)

( * ) Notice: Subject to any disclaimer, the term of this patent is extended or adjusted under 35 U.S.C. 154(b) by 308 days.

(21) Appl. No.: 15/178,622

(22) Filed: Jun. 10, 2016

(65) Prior Publication Data

US 2017/0028258 A1    Feb. 2, 2017

(30) Foreign Application Priority Data

Jul. 31, 2015 (CN) .......................... 2015 1 0462845

(51) Int. Cl.
  A63B 24/00 (2006.01)
  A63B 21/00 (2006.01)
  G06F 19/00 (2018.01)
  G16H 20/30 (2018.01)

(52) U.S. Cl.
  CPC ...... A63B 24/0062 (2013.01); A63B 21/4037 (2015.10); G06F 19/00 (2013.01); G16H 20/30 (2018.01)

(58) Field of Classification Search
  USPC ....................................................... 702/139
  See application file for complete search history.

(56) References Cited

U.S. PATENT DOCUMENTS

| | | | |
|---|---|---|---|
| 6,719,708 | B1 | 4/2004 | Jansen |
| 2001/0034288 | A1 | 10/2001 | Howlett-Campanella |
| 2006/0171570 | A1 | 8/2006 | Brendley et al. |
| 2006/0258512 | A1 | 11/2006 | Nicolas |
| 2007/0123391 | A1 | 5/2007 | Shin et al. |
| 2007/0179360 | A1* | 8/2007 | Mikat .............. A61B 5/103 |
| | | | 600/300 |
| 2010/0035727 | A1 | 2/2010 | Brunner |
| 2010/0041516 | A1 | 2/2010 | Kodama |
| 2011/0054358 | A1 | 3/2011 | Kim et al. |

(Continued)

FOREIGN PATENT DOCUMENTS

| | | |
|---|---|---|
| CN | 1250159 C | 4/2006 |
| CN | 1913940 A | 2/2007 |

(Continued)

OTHER PUBLICATIONS

Extended European Search Report of European Patent Application No. 16166981.7, from the European Patent Office, dated Dec. 16, 2016.

(Continued)

*Primary Examiner* — Paul D Lee
(74) *Attorney, Agent, or Firm* — Finnegan, Henderson, Farabow, Garrett & Dunner LLP

(57) ABSTRACT

The disclosure relates to a method and device for recording exercise. The method is used in a mat, and includes: determining critical force areas of a user on the mat; determining exercise status of the user on the mat according to variations of pressure values at the critical force areas, the pressure values being measured by pressure sensors at the critical force areas; and sending exercise information to a terminal, the exercise information including the exercise status.

15 Claims, 8 Drawing Sheets

(56) References Cited

U.S. PATENT DOCUMENTS

| | | |
|---|---|---|
| 2012/0015334 A1 | 1/2012 | Hamilton |
| 2012/0058861 A1* | 3/2012 | Satut ................ A63B 6/00 482/8 |
| 2013/0090571 A1* | 4/2013 | Nourani ............ A61B 5/103 600/587 |
| 2013/0116852 A1 | 5/2013 | Dijk et al. |
| 2014/0041001 A1 | 2/2014 | Cheung |
| 2015/0052253 A1 | 2/2015 | Johnson et al. |

FOREIGN PATENT DOCUMENTS

| | | |
|---|---|---|
| CN | 101677786 A | 3/2010 |
| CN | 102421403 A | 4/2012 |
| CN | 102770187 A | 11/2012 |
| CN | 103298527 A | 9/2013 |
| CN | 103417218 A | 12/2013 |
| CN | 203749393 U | 8/2014 |
| CN | 104537132 A | 4/2015 |
| CN | 105107134 A | 12/2015 |
| EP | 1662406 A1 | 5/2006 |
| GB | 2399767 A | 9/2004 |
| JP | S 60-166363 A | 8/1985 |
| JP | 2001-149185 A | 6/2001 |
| JP | 2007-151117 A | 6/2007 |
| JP | 2010-42126 A | 2/2010 |
| JP | 2013-541745 A | 11/2013 |
| JP | 2015100568 A | 6/2015 |
| SU | 403975 A1 | 10/1973 |
| TW | 201407392 A | 2/2014 |
| WO | WO 2011/105419 A1 | 9/2011 |
| WO | WO 2015/003211 A1 | 1/2015 |
| WO | WO-2015/003211 A1 | 1/2015 |

OTHER PUBLICATIONS

Misaki, A. et al., "Body Pressure Sensing Mattress for Bedsore Prevention," SEI Technical Review, No. 78, dated Apr. 2014, pp. 95-98.

Office Action for Russian Application No. 2016110069/14(015896), mailed from the Russian Federal Service for Intellectual Property on May 19, 2017.

Office Action issued in European Patent Application No. 16166981.7, dated Sep. 4, 2017.

Office Action for Russian Application No. 2016110069/14(015896), mailed from the Russian Federal Service for Intellectual Property on Sep. 27, 2017.

Sundholm M. et al., "Smart-Mat: Recognizing and Counting Gym Exercises with Low-cost Resistive Pressure Sensing Matrix", ACM, Seattle, WA, US, Sep. 13-17, 2014.

"SmartMat—the world's first "smart" mat for yoga", retrievable at url: http://medgadgets.ru/fitness/smartmat-pervyj-v-mire-umnyj-kovrik-dlya-jogi.html, dated Oct. 14, 2014.

Extended European Search Report issued in European Application No. 16166981.7, mailed from the European Patent Office dated Dec. 16, 2016.

International Search Report of PCT/CN2015/098437, mailed from the State Intellectual Property Office of China dated Apr. 28, 2016.

* cited by examiner

Status 1          Status 2

500

METHODS AND DEVICES FOR RECORDING EXERCISE

CROSS-REFERENCE TO RELATED APPLICATION

This application is based upon and claims priority to Chinese Patent Application No. 201510462845.7, filed Jul. 31, 2015, the entire contents of which are incorporated herein by reference.

TECHNICAL FIELD

The present disclosure generally relates to the field of computer technology and, more particularly, to methods and devices for recording exercise.

BACKGROUND

With the growing enthusiasm towards physical exercises and healthy lifestyles, more and more attention has been given to electronic devices, such as terminals and wearable devices, that can provide statistical information about physical exercise. A user may carry such an electronic device during physical exercise to record the user's actions. For example, when the user is walking or running, the electrical device may count the steps of the user, the walking/running distance, and the calorie consumption of the user, etc.

SUMMARY

According to a first aspect of the present disclosure, there is provided a method for use in a mat, comprising: determining critical force areas of a user on the mat; determining exercise status of the user on the mat according to variations of pressure values at the critical force areas, the pressure values being measured by pressure sensors at the critical force areas; and sending exercise information to a terminal, the exercise information including the exercise status.

According to a second aspect of the present disclosure, there is provided a device, comprising: a processor; a memory for storing instructions executable by the processor; wherein the processor is configured to perform: determining critical force areas of a user on the mat; determining exercise status of the user on the mat according to variations of pressure values at the critical force areas, the pressure values being measured by pressure sensors at the critical force areas; and sending exercise information to a terminal, the exercise information including the exercise status.

According to a third aspect of the present disclosure, there is provided a non-transitory computer-readable storage medium storing instructions that, when executed by a processor of a device, cause the device to perform: determining critical force areas of a user on the mat; determining exercise status of the user on the mat, according to variations of pressure values at the critical force areas, the pressure values being measured by pressure sensors at the critical force areas; and sending exercise information to the terminal, the exercise information including the exercise status.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments consistent with the invention and, together with the description, serve to explain the principles of the invention.

DETAILED DESCRIPTION

Reference will now be made in detail to exemplary embodiments, examples of which are illustrated in the accompanying drawings. The following description refers to the accompanying drawings in which same numbers in different drawings represent same or similar elements unless otherwise described. The implementations set forth in the following description of exemplary embodiments do not represent all implementations consistent with the invention. Instead, they are merely examples of devices and methods consistent with aspects related to the invention as recited in the appended claims.

Figure 1:
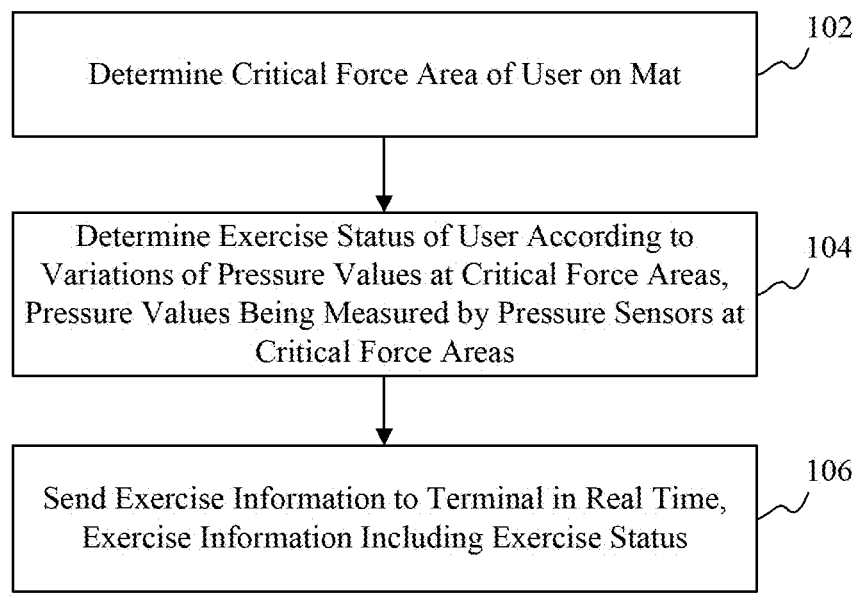
FIG. 1 is a flowchart of a method for recording exercise, according to an exemplary embodiment.

FIG. 1 is a flowchart of a method 100 for recording exercise, according to an exemplary embodiment. For example, the method 100 may be used in a mat. The mat has pressure sensors evenly distributed thereon and may be wirelessly connected to a terminal. As shown in FIG. 1, the method 100 includes the following steps.

In step 102, the mat determines critical force areas of a user on the mat.

In step 104, the mat determines exercise status of the user, according to the variations of pressure values at the critical force areas. The pressure values are measured by pressure sensors at the respective critical force areas.

In step 106, the mat sends exercise information to the terminal in real time. The exercise information includes the exercise status.

According to the method 100, the mat determines the critical force areas of a user on the mat. The mat then determines the exercise status of the user, according to the variations of the pressure values at the critical force areas. The pressure values are measured by the pressure sensors at these critical force areas. The mat further sends the real-time exercise information to the terminal. The exercise information includes the exercise status. In this manner, the terminal can record the physical exercise that the user is doing. Therefore, the method 100 solves the limitation in conventional electronic devices that the physical exercises other than walking or running cannot be recorded, and enriches the ways in which a user does physical exercise.

Figure 2A:
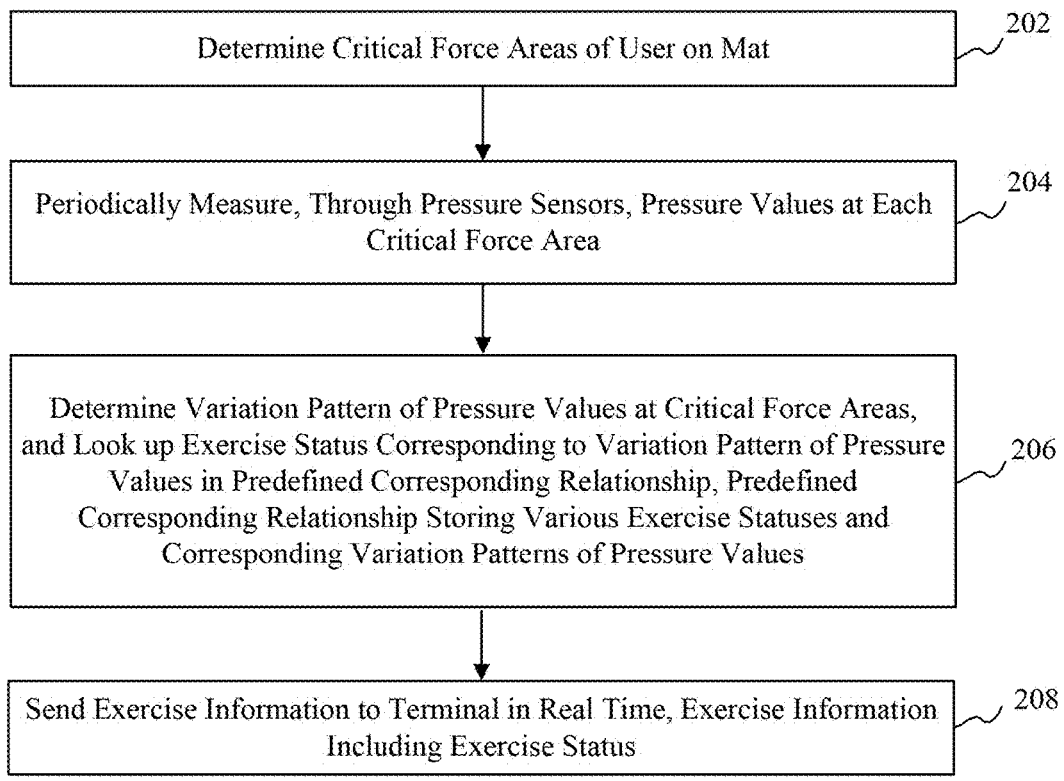
FIG. 2A is a flowchart of a method for recording exercise, according to an exemplary embodiment.

FIG. 2A is a flowchart of a method 200 for recording exercise, according to an exemplary embodiment. For example, the method 200 may be used in a mat. The mat has pressure sensors evenly distributed thereon and may be wirelessly connected to a terminal. As shown in FIG. 2A, the method 200 includes the following steps.

In step 202, the mat determines critical force areas of a user on the mat.

The critical force areas are the areas on the mat that touch the user's body when the user is doing physical exercise on the mat. For example, the critical force areas may include critical force areas corresponding to the head, feet, hip, and arms of the user, respectively (referred to as "head force area," "foot force area," "hip force area," and "arm force area," respectively).

The mat may be triggered to determine the critical force areas in various manners. In one embodiment, the mat has one or more triggering buttons. When the user presses a triggering button, the mat is triggered to determine the critical force areas. In another embodiment, one or more triggering buttons are provided on a terminal. When the user presses a triggering button, the terminal sends a triggering signal to the mat. The triggering signal is configured to trigger the mat to determine the critical force areas. In yet another embodiment, after the user lies down on the mat, the mat detects whether the user remains still for a specified period of time, by monitoring, through pressure sensors, the pressure on the mat. If it is detected that the user remains still for the specified period of time, the mat starts to determine the critical force areas.

Because different types of exercises are featured with different critical force areas, the mat may determine the critical force areas according to the types of the exercises supported by the mat. For example, if the exercise to be recorded is sit-up, the corresponding critical force areas include the head force area and the foot force area. Accordingly, the mat only needs to determine these two critical force areas for recording the sit-up. For another example, if the exercise to be recorded is push-up, the corresponding critical force areas include the arm force area and the foot force area. Accordingly, the mat only needs to determine these two critical force areas for recording the push-up.

Generally, the more critical force areas the mat has, the more accurately the mat can determine the exercise status. Therefore, in exemplary embodiments, the mat may be configured to determine all the available critical force areas and determine the exercise status based on all the critical force areas, regardless the type of the exercise and regardless whether the exercise corresponds to all the critical force areas. Here, the term "all the critical force areas" refers to the collection of the head force area, the foot force area, the hip force area, and the arm force area.

In exemplary embodiments, the mat may determine all the critical force areas according to the pressure values measured by the pressure sensors. Alternatively, the mat may first determine some critical force areas according to the pressure values, and then determine all the critical force areas based on the previously-determined critical force areas. In one embodiment, the determining of the critical force areas of the user on the mat may include: when the user is lying on the mat, determining n critical force areas of the user on the mat according to the pressure values measured by the pressure sensors, wherein n≥2; and determining all the critical force areas of the user on the mat based on the n critical force areas.

The following description provides the detailed processes to determine the n critical force areas and all the critical force areas, when n=2, 3, and 5, respectively.

When n=2, the process of determining n critical force areas includes: identifying, in a longitudinal direction of the mat, two critical force areas that are separated by the longest distance and have non-zero pressure values; from the two identified critical force areas separated by the longest distance in the longitudinal direction, determining the critical force area with the higher pressure value to be the head force area, and determining the critical force area with the lower pressure value to be the foot force area.

The head is at the uppermost position of the user's body, and the feet correspond to the lowest position of the body. Therefore, when the user lies on the mat, the two force areas separated by the longest distance in the longitudinal direction of the mat and with non-zero pressure values may correspond to the head force area and the foot force area, respectively. Furthermore, when the user lies on the mat, the pressure created by the head is higher than the pressure created by the feet. Thus, the mat may compare the pressure values of the two identified force areas, and determine the force area with the higher pressure value to be the head force area, and the force area with the lower pressure to be the foot force area.

After the head force area and the foot force area are determined, the determining of all the critical force areas based on the n critical force areas includes: determining the user's leg-to-body ratio (or length of legs), according to the user information pre-stored in the terminal; determining the hip force area according to the leg-to-body ratio (or the length of the legs), the location of the head force area, and the location of the foot force area; determining a predefined area, at each side of a line connecting the head force point and the hip force point, to be an arm force area; and determining the head force area, the arm force areas, the hip force area, and the foot force area to be all the critical force areas of the user on the mat.

A user may input and store the user information in the terminal in advance. The user information may include the user's gender, height, weight, length of legs, leg-to-body ratio, or the like. The terminal sends the user information to the mat. The mat determines the hip force area according to the length of legs and/or the leg-to-body ratio, after determining the head force area and the foot force area. Here, the leg-to-body ratio is the ratio of the height of perineum over the height of the whole body. In one embodiment, the mat and/or terminal may determine the leg-to-body ratio based on other user information, such as gender. For example, the average leg-to-body ratios of Asian male and female are 45.70% and 44.90%, respectively. The average leg-to-body ratios of male and female in western countries are 47.68% and 47.34%, respectively.

For example, if the mat determines the distance from the head force area to the foot force area is 1.6 meters and the length of the legs is 0.7 meter, the mat may determine that the hip force area is 0.7 meter away from the foot force area in the longitudinal direction of the mat. For another example, if the mat determines that the distance from the head force area to the foot force area is 1.6 meters and the pre-stored leg-to-body ratio as 44.90%, the mat calculates the length of legs according to the equation: the length of legs=44.9%*1.6=0.7 meter. Accordingly, the mat determines that the hip force area is 0.7 meter away from the foot force area in the longitudinal direction of the mat.

The arms are located at both sides of the upper body of the user. Thus, after determining the head force area and hip force area, the mat may further determine each arm force area as a predefined area at each side of a line connecting the head force area and the hip force area. Each predefined area has a length longer than or equal to the length of an arm of the user. For example, the mat may determine a 1-meter area at each side of the line connecting the head force area and the hip force area to be the respective arm force area.

When n=3, the process of determining n critical force areas includes: identifying, in the longitudinal direction of the mat, two critical force areas that are separated by the longest distance and have non-zero pressure values; determining, from the two critical force areas separated by the longest distance in the longitudinal direction, the critical force area with the higher pressure value to be the head force area, and the critical force area with the lower pressure value to be the foot force area; and determining, in the longitudinal direction of the mat, the critical force area with the highest pressure value to be the hip force area.

Because the hip creates the highest pressure when the user is lying on the mat, the mat may determine the force area with the highest pressure value in the longitudinal direction to be the hip force area. The detailed method for the mat to determine the head force area and the foot force area is the same as the method described in the case of n=2, which is not elaborated herein.

After the head force area, the hip force area, and the foot force area are determined, the determining, based on the n critical force areas, of all the critical force areas of the user on the mat includes: determining a predefined area at each side of a line connecting the head force area and the hip force area to be an arm force area; and determining the head force area, the arm force areas, the hip force area, and the foot force area to be all the critical force areas of the user on the mat.

The detailed method for the mat to determine the arm force areas is the same as the method described in the case of n=2, which is not elaborated herein.

When n=5, the process of determining n critical force areas includes: identifying, in the longitudinal direction of the mat, two critical force areas that are separated by the longest distance and have non-zero pressure values; determining, from the two identified critical force areas separated by the longest distance in the longitudinal direction, the critical force area with the higher pressure value to be the head force area, and the critical force area with the lower pressure value to be the foot force area; determining the force area with the highest pressure value in the longitudinal direction of the mat to be the hip force area; identifying, in the width direction of the mat, two critical force areas that are separated by the longest distance and have non-zero pressure values; and determining the two identified force areas in the width direction to be the hand force areas.

The force areas of the two hands have the same pressure value. The detailed method for the mat to determine the head force area, the hip force area, and the foot force area is the same as the method described that in the case of n=2, which is not elaborated herein.

After the head force area, the hip force area, the foot force area, and the hand force areas are determined, the determining, based on the n critical force areas, of all the critical force areas of the user on the mat includes: determining a predefined area extending from each hand force area to the head force area to be an arm force area; and determining the head force area, the arm force areas, the hip force area, and the foot force area to be all the critical force areas of the user on the mat.

In step 204, the mat periodically measures, through the pressure sensors, the pressure values at each critical force area.

In step 206, the mat determines the variation pattern of the pressure values at the critical force areas, and looks up, in a predefined corresponding relationship, the exercise status corresponding to the variation pattern. The predefined corresponding relationship stores various exercise statuses and the corresponding variation patterns of pressure values.

The variation patterns of pressure values corresponding to several common exercises are described below.

Figure 2B:
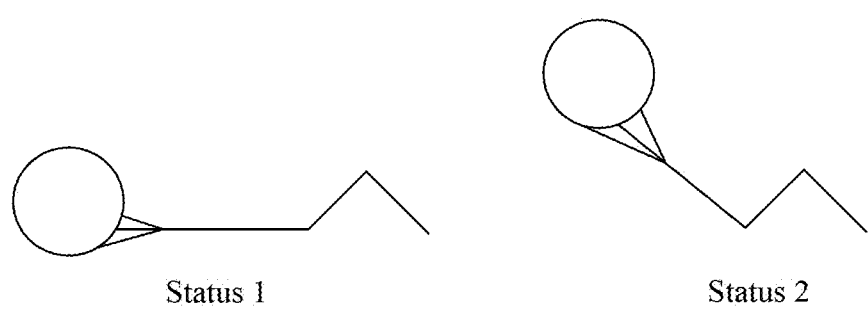
FIG. 2B is a schematic diagram illustrating a sit-up, according to an exemplary embodiment.

FIG. 2B is a schematic diagram illustrating a sit-up, according to an exemplary embodiment. Referring to FIG. B, when the user is in status 1, i.e., lying on the back, the pressure values at the head force area, the hip force area, and the foot force area do not change, and the pressure values at the arm force areas are zero. When the user is in status 2, i.e., sitting up, the pressure value at the foot force area does not change, the pressure value at the hip force area increases, and the pressure values at the arm force areas and the head force area are zero. Such variation pattern of pressure values is paired with sit-up in the predefined corresponding relationship.

Figure 2C:
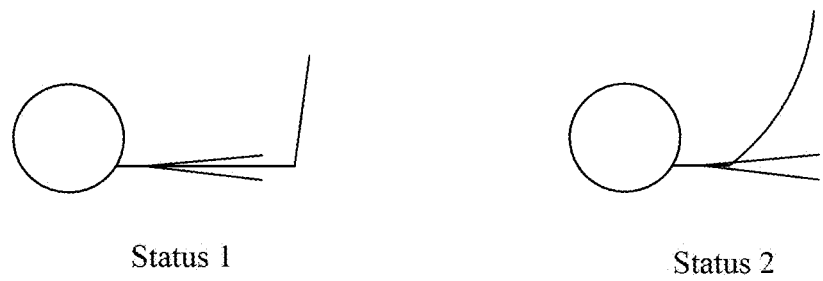
FIG. 2C is a schematic diagram illustrating a lying leg raise, according to an exemplary embodiment.

FIG. 2C is a schematic diagram illustrating a lying leg raise, according to an exemplary embodiment. Referring to FIG. 2C, when the user is in status 1, i.e., lying on the back, the pressure values at the arm force areas, the head force area, and the hip force area do not change, and the pressure value at the foot force area is zero. When the user is in status 2, i.e., raising the legs, the pressure values at the arm force areas and the head force area do not change, and the pressure values at the hip force area and the foot force area are zero. Such variation pattern of pressure values is paired with lying leg raise in the predefined corresponding relationship.

Figure 2D:
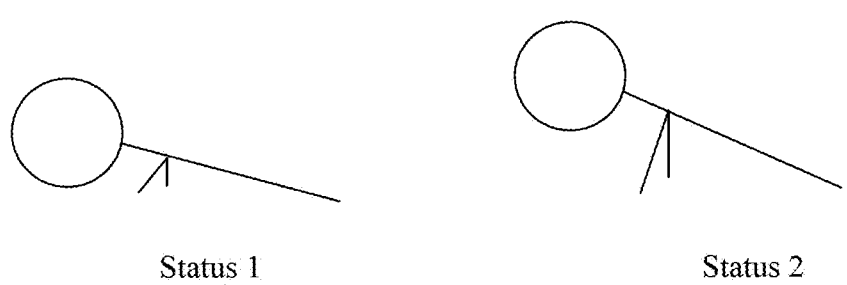
FIG. 2D is a schematic diagram illustrating a push-up, according to an exemplary embodiment.

FIG. 2D is a schematic diagram illustrating a push-up, according to an exemplary embodiment. Referring to FIG. 2D, when the user is in status 1, i.e., in a prone position, the pressure values at the arm force areas and the foot force area do not change, and the pressure values at the head force area and the hip force area are zero. When the user is in status 2, i.e., pushing up, the pressure values at the arm force areas and the foot force area increase, and the pressure values at the head force area and the hip force area are zero. Such variation pattern of pressure values is paired with push-up in the predefined corresponding relationship.

In step 208, the mat sends exercise information to the terminal. The exercise information includes the exercise status.

In one embodiment, the mat includes a display. The mat may display the exercise information on the display. The user may be informed about the user's exercise status according to the displayed information. In another embodiment, the mat does not include a display. The mat may send the exercise information to the terminal in real time. The terminal records the exercise status of the user according to the exercise information, and the user may check the exercise status on the terminal.

In exemplary embodiments, the mat may be provided with two transmission modes for transmitting the exercise information to the terminal. The two transmission modes are described below respectively.

In the first transmission mode, the mat generates the exercise information and sends the exercise information to the terminal in real time. The terminal determines, according to the exercise status, the body parts trained by the exercise.

The terminal may pre-store a corresponding relationship between various exercise statuses and the body parts trained by each exercise. After receiving the exercise status from the mat, the terminal may determine the trained body parts based on the corresponding relationship, and provide the determining result to the user. For example, the corresponding relationship may indicate that the body part trained by sit-up is the belly, and the body part trained by push-up is the chest, etc.

In the second transmission mode, the mat acquires the number of certain movements performed by the user during the exercise, and generates the exercise information. The exercise information includes the exercise status and the number of movements. The mat sends the exercise information to the terminal in real time. The terminal then calculates the total energy consumption of the user based on the number of the movements and the energy consumption of a single movement.

The mat may also determine the number of movements based on the variation pattern of pressure values, and send the exercise information, including the exercise status and the number of movements, to the terminal in real time. The terminal queries the calories that a single movement consumes, and multiplies the number of movements by the calories for a single movement to obtain the total calorie consumption of the user.

In addition to determining the trained body parts and total calorie consumption based on the exercise information, the terminal may also make other determinations based on the exercise information. The present disclosure does not limit the usage of the exercise information.

Figure 3:
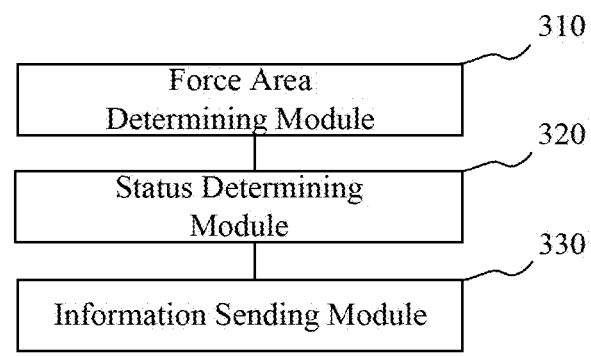
FIG. 3 is a block diagram of a device for recording exercise, according to an exemplary embodiment.

FIG. 3 is a block diagram of a device 300 for recording exercise, according to an exemplary embodiment. For example, the device 300 may be implemented as part or whole of a mat. The mat has pressure sensors evenly distributed thereon and may be wirelessly connected to a terminal. As shown in FIG. 3, the device 300 includes a force area determining module 310, a status determining module 320, and an information sending module 330.

The force area determining module 310 is configured to determine critical force areas of a user on the mat.

The status determining module 320 is configured to determine the exercise status of the user according to the variations of the pressure values at the critical force areas. The pressure values are measured by pressure sensors at the respective critical force areas.

The information sending module 330 is configured to send the exercise information to the terminal in real time. The exercise information includes the exercise status.

Figure 4:
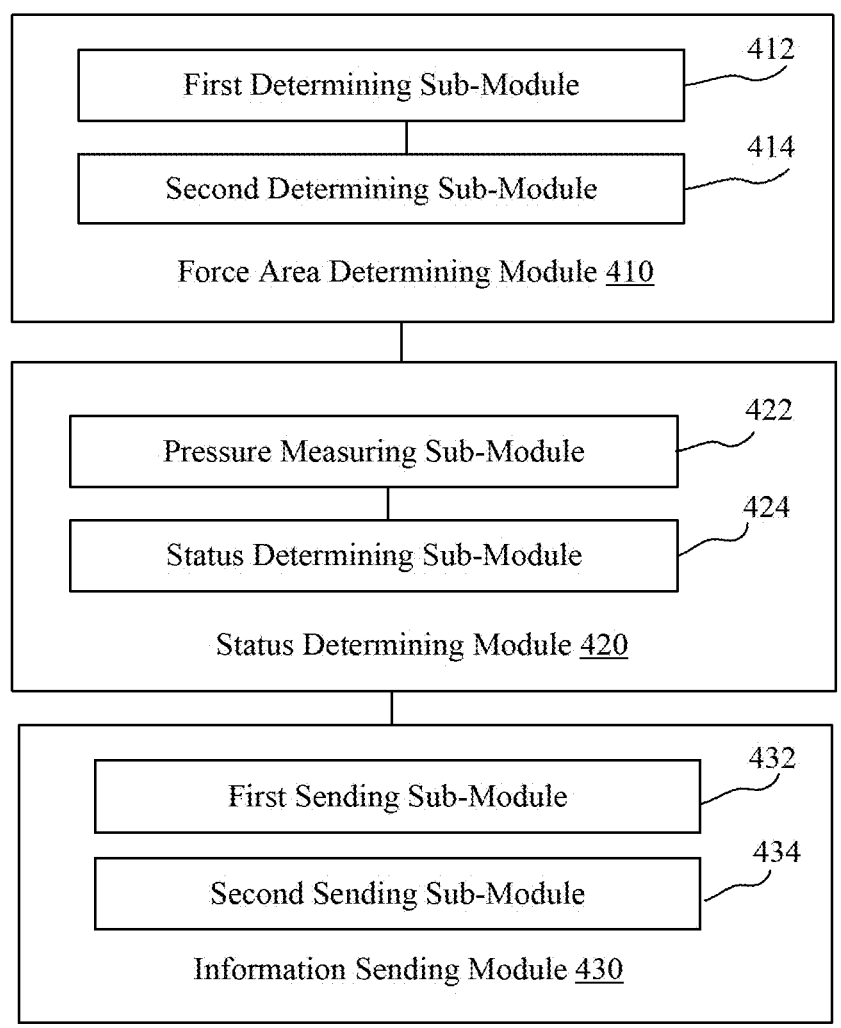
FIG. 4 is a block diagram of a device for recording exercise, according to an exemplary embodiment.

FIG. 4 is a block diagram of a device 400 for recording exercise, according to an exemplary embodiment. For example, the device 400 may be implemented as part or whole of a mat. The mat has pressure sensors evenly distributed thereon and may be wirelessly connected to a terminal. As shown in FIG. 4, the device 400 may include a force area determining module 410, a status determining module 420, and an information sending module 430, similar to the force area determining module 310, the status determining module 320, and the information sending module 330, respectively (FIG. 3).

In some embodiments, the force area determining module 410 further includes a first determining sub-module 412 and a second determining sub-module 414.

The first determining sub-module 412 is configured to determine n critical force areas of the user on the mat, according to the pressure values measured by the pressure sensors when the user is lying on the mat. Here n≥2.

The second determining sub-module 414 is configured to determine all the critical force areas of the user on the mat, based on the n critical force areas determined by the first determining sub-module 412.

In some embodiments, the first determining sub-module 412 is further configured to perform the following operations.

When n=2, the first determining sub-module 412 is configured to perform: identify, in the longitudinal direction of the mat, two critical force areas that are separated by the longest distance and have non-zero pressure values; determine, from the two critical force areas separated by the longest distance in the longitudinal direction of the mat, the critical force area with the higher pressure value to be the head force area, and the critical force area with the lower pressure value to be the foot force area.

When n=3, the first determining sub-module 412 is configured to: identify, in the longitudinal direction of the mat, two critical force areas that are separated by the longest distance and have non-zero pressure values; determine, from the two critical force areas separated by the longest distance in the longitudinal direction, the critical force area with the higher pressure value to be the head force area, and the critical force area with the lower pressure value to be the foot force area; and determine, in the longitudinal direction of the mat, the critical force area with the highest pressure value to be the hip force area.

When n=5, the first determining sub-module 412 is configured to: identify, in the longitudinal direction of the mat, two critical force areas that are separated by the longest distance and have non-zero pressure values; determine, from the two identified critical force areas separated by the longest distance in the longitudinal direction, the critical force area with the higher pressure value to be the head force area, and the critical force area with the lower pressure value to be the foot force area; determine the force area with the highest pressure value in the longitudinal direction of the mat to be the hip force area; identify, in the width direction of the mat, two critical force areas that are separated by the longest distance and have non-zero pressure values; and determine the two identified force areas in the width direction to be the hand force areas.

Corresponding to the above-described operations by the first determining sub-module 412, the second determining sub-module 414 is further configured to perform the following operations.

When n=2, the second determining sub-module 414 is further configured to: determine the user's leg-to-body ratio (or length of legs), according to the user information pre-stored in the terminal; determine the hip force area according to the leg-to-body ratio (or the length of legs), the location of the head force area, and the location of the foot force area; determine a predefined area, at each side of a line connecting the head force point and the hip force point, to be an arm force area; and determine the head force area, the arm force areas, the hip force area, and the foot force area to be all the critical force areas of the user on the mat.

When n=3, the second determining sub-module 414 is further configured to: determine a predefined area at each side of a line connecting the head force area and the hip force area to be an arm force area; and determine the head force area, the arm force areas, the hip force area, and the foot force area to be all the critical force areas of the user on the mat.

When n=5, the second determining sub-module 414 is further configured to: determine a predefined area extending from each hand force areas to the head force area to be an arm force area; and determine the head force area, the arm force areas, the hip force area, and the foot force area to be all the critical force areas of the user on the mat.

In some embodiments, the status determining sub-module 420 further includes a pressure measuring sub-module 422 and a status determining sub-module 424.

The pressure measuring sub-module 422 is configured to measure the pressure values of the pressure sensors at each critical force area periodically.

The status determining sub-module 424 is configured to determine the variation pattern of the pressure values at the critical force areas, and look up, in a predefined corresponding relationship, the exercise status corresponding to the variation pattern of the pressure values. The corresponding relationship stores various exercise statuses and the corresponding variation of pressure values.

In some embodiments, the information sending module 430 further includes a first sending sub-module 432 and a second sending sub-module 434.

The first sending sub-module 432 is configured to generate exercise information and send the exercise information to the terminal in real time. The exercise information includes the exercise status. The terminal determines the body parts trained by the exercise, according to the exercise status.

The second sending sub-module 434 is configured to acquire the number of certain movement, generate the exercise information, and send the exercise information to the terminal in real time. The exercise information includes the exercise status and the number of the movement. The terminal computes the total energy consumed by the user during the exercise, based on the number of the movement and the energy consumption of a single movement.

Consistent with the disclosed methods and devices, a mat determines critical force areas of a user on the mat. The mat also determines the exercise status of the user according to the variations of the pressure values at the critical force areas. The pressure values are measured by pressure sensors at the critical force areas. The mat further sends exercise information, including the exercise status, to a terminal in real time. In this manner, the terminal can record the physical exercise that the user is doing. Therefore, the disclosed devices and methods solve the limitation in conventional electronic devices that the physical exercises other than walking or running cannot be recorded, and enrich the ways in which a user does physical exercise.

Moreover, by determining the hip force area based on the leg-to-body ratio, the head force area, and the foot force area, the disclosed methods and devices improve the accuracy of determining the critical force areas.

Further, consistent with the disclosed methods and devices, the mat sends the exercise information to the terminal in real time, such that the terminal may determine the body parts trained by the exercise and/or calculate the energy consumption of the user. Therefore, a comprehensive exercise record may be provided to the user.

With respect to the devices in the above embodiments, the specific manners of the individual modules and sub-modules in performing the respective operations therein have been described in details in the embodiments regarding the methods, which will not be elaborated herein.

Figure 5:
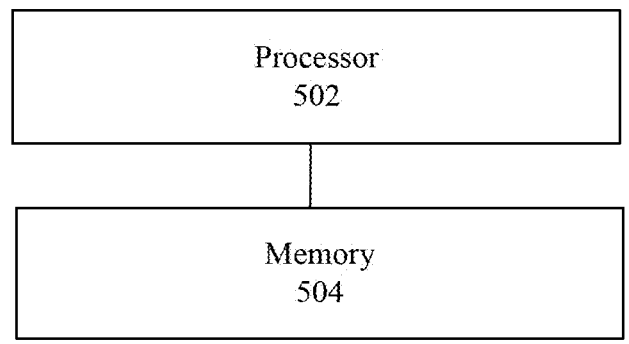
FIG. 5 is a block diagram of a device for recording exercise, according to an exemplary embodiment.

FIG. 5 is a block diagram of a device 500 for recording exercise, according to an exemplary embodiment. For example, the device 500 may be used in a mat. Referring to FIG. 5, the device 500 includes a processor 502 and a memory 504 for storing instructions executable by the processor 502. The processor 502 is configured to perform the above described methods for recording exercise.

Other embodiments of the invention will be apparent to those skilled in the art from consideration of the specification and practice of the disclosures herein. This application is intended to cover any variations, uses, or adaptations of the disclosure following the general principles thereof and including such departures from the present disclosure as come within known or customary practice in the art. It is intended that the specification and examples be considered as exemplary only, with a true scope and spirit of the invention being indicated by the following claims.

It will be appreciated that the inventive concept is not limited to the exact construction that has been described above and illustrated in the accompanying drawings, and that various modifications and changes can be made without departing from the scope thereof. It is intended that the scope of the invention only be limited by the appended claims.

What is claimed is:

1. A method for use in a mat, comprising:
   determining critical force areas of a user on the mat;
   determining exercise status of the user on the mat according to variations of pressure values at the critical force areas, the pressure values being measured by pressure sensors at the critical force areas, wherein the exercise status of the user comprises a type of physical exercise taken by the user; and
   sending exercise information to a terminal, the exercise information including the exercise status,
   wherein the determining of the exercise status of the user on the mat, according to the variations of the pressure values at the critical force areas comprises:
   periodically measuring, through the pressure sensors, the pressure values at the critical force areas;
   determining a variation pattern of the pressure values at the critical force areas; and
   determining, according to a predefined corresponding relationship between exercise statuses and variation patterns of the pressure values, the exercise status corresponding to the variation pattern of the pressure values.

2. The method of claim 1, wherein the determining of the critical force areas of the user on the mat comprises:
   determining a subset of the critical force areas, including n critical force areas, of the user on the mat, according to the pressure values measured by the pressure sensors when the user is lying on the mat, wherein n≥2; and
   determining, based on the n critical force areas, all of the critical force areas of the user on the mat.

3. The method of claim 2, wherein the determining of the n critical force areas of the user on the mat, according to the pressure values measured by the pressure sensors when the user is lying on the mat, comprises:
   when n=2,
      identifying, in a longitudinal direction of the mat, two critical force areas that are separated by a longest distance and have different non-zero pressure values; and
      determining, from the two critical force areas separated by the longest distance in the longitudinal direction of the mat, the critical force area with the higher pressure value to be a head force area, and the critical force area with the lower pressure value to be a foot force area;
   when n=3,
      identifying, in a longitudinal direction of the mat, two critical force areas that are separated by a longest distance and have different non-zero pressure values;
      determining, from the two critical force areas separated by the longest distance in the longitudinal direction of the mat, the critical force area with the higher pressure value to be a head force area, and the critical force area with the lower pressure value to be a foot force area; and determining, in the longitudinal direction of the mat, a force area with a highest pressure value to be a hip force area; and when n=5,
identifying, in a longitudinal direction of the mat, two critical force areas that are separated by a longest distance and have different non-zero pressure values;

determining, from the two critical force areas separated by the longest distance in the longitudinal direction of the mat, the critical force area with the higher pressure value to be a head force area, and the critical force area with the lower pressure value to be a foot force area;

determining, in the longitudinal direction of the mat, a force area with a highest pressure value to be a hip force area;

identifying, in a width direction of the mat, two critical force areas that are separated by a longest distance and have non-zero pressure values; and determining the two critical force areas separated by the longest distance in the width direction of the mat to be hand force areas.

4. The method of claim 3, wherein when n=2, the determining, based on the n critical force areas, of all of the critical force areas of the user on the mat comprises:
determining a leg-to-body ratio of the user according to user information stored in the terminal;
determining a hip force area according to the leg-to-body ratio, a location of the head force area, and a location of the foot force area;
determining a predefined area at each side of a line connecting the head force area and the hip force area to be an arm force area; and
determining the head force area, the arm force areas, the hip force area, and the foot force area to be all the critical force areas of the user on the mat.

5. The method of claim 3, wherein when n=3, the determining, based on the n critical force areas, of all the critical force areas of the user on the mat comprises:
determining a predefined area at each side of a line connecting the head force area and the hip force area to be an arm force area; and
determining the head force area, the arm force areas, the hip force area, and the foot force area to be all the critical force areas of the user on the mat.

6. The method of claim 3, wherein when n=5, the determining, based on the n critical force areas, of all the critical force areas of the user on the mat comprises:
determining an area extending from each hand force area to the head force area to be an arm force area; and
determining the head force area, the arm force areas, the hip force area, and the foot force area to be all the critical force areas of the user on the mat.

7. The method of claim 1, wherein the sending of the exercise information to the terminal includes at least one of:
generating the exercise information in real time, and sending the exercise information to the terminal in real time, wherein the terminal is configured to determine, according to the exercise status, body parts trained by the user during the exercise; or
acquiring a number of a movement performed by the user, generating in real time the exercise information including the exercise status and the number of the movement, and sending the exercise information to the terminal in real time, wherein the terminal is configured to compute a total energy consumption of the user based on the number of the movement and an energy consumption caused by a single movement.

8. A device, comprising:
a processor;
a memory for storing instructions executable by the processor;
wherein the processor is configured to perform:
determining critical force areas of a user on a mat;
determining exercise status of the user on the mat according to variations of pressure values at the critical force areas, the pressure values being measured by pressure sensors at the critical force areas, wherein the exercise status of the user comprises a type of physical exercise taken by the user; and
sending exercise information to a terminal, the exercise information including the exercise status,
wherein the processor is further configured to perform the following operations to perform the determining exercise status of the user on the mat:
periodically measuring, through the pressure sensors, the pressure values at the critical force areas;
determining a variation pattern of the pressure values at the critical force areas; and
determining, according to a predefined corresponding relationship between exercise statuses and variation patterns of the pressure values, the exercise status corresponding to the variation pattern of the pressure values.

9. The device of claim 8, wherein the processor is further configured to perform:
determining a subset of the critical force areas, including n critical force areas of the user on the mat, according to the pressure values measured by the pressure sensors when the user is lying on the mat, wherein n≥2; and
determining, based on the n critical force areas, all the critical force areas of the user on the mat.

10. The device of claim 9, wherein the processor is further configured to perform:
when n=2,
identifying, in a longitudinal direction of the mat, two critical force areas that are separated by a longest distance and have different non-zero pressure values; and
determining, from the two critical force areas separated by the longest distance in the longitudinal direction of the mat, the critical force area with the higher pressure value to be a head force area, and the critical force area with the lower pressure value to be a foot force area;

when n=3,
identifying, in a longitudinal direction of the mat, two critical force areas that are separated by a longest distance and have different non-zero pressure values;
determining, from the two critical force areas separated by the longest distance in the longitudinal direction of the mat, the critical force area with the higher pressure value to be a head force area, and the critical force area with the lower pressure value to be a foot force area; and
determining, in the longitudinal direction of the mat, a force area with a highest pressure value to be a hip force area; and when n=5,
identifying, in a longitudinal direction of the mat, two critical force areas that are separated by a longest distance and have different non-zero pressure values;

determining, from the two critical force areas separated by the longest distance in the longitudinal direction of the mat, the critical force area with the higher pressure value to be a head force area, and the critical force area with the lower pressure value to be a foot force area;

determining, in the longitudinal direction of the mat, a force area with a highest pressure value to be a hip force area;

identifying, in a width direction of the mat, two critical force areas that are separated by a longest distance and have non-zero pressure values; and determining the two critical force areas separated by the longest distance in the width direction of the mat to be hand force areas.

11. The device of claim 10, wherein when n=2, the processor is further configured to perform:

determining a leg-to-body ratio of the user according to user information stored in the terminal;

determining a hip force area according to the leg-to-body ratio, a location of the head force area, and a location of the foot force area;

determining a predefined area at each side of a line connecting the head force area and the hip force area to be an arm force area; and determining the head force area, the arm force areas, the hip force area, and the foot force area to be all the critical force areas of the user on the mat.

12. The device of claim 10, wherein when n=3, the processor is further configured to perform:

determining a predefined area at each side of a line connecting the head force area and the hip force area to be an arm force area; and determining the head force area, the arm force areas, the hip force area, and the foot force area to be all the critical force areas of the user on the mat.

13. The device of claim 10, wherein when n=5, the processor is further configured to perform:

determining an area extending from each hand force area to the head force area to be an arm force area; and determining the head force area, the arm force areas, the hip force area, and the foot force area to be all the critical force areas of the user on the mat.

14. The device of claim 8, wherein the processor is further configured to perform:

generating the exercise information in real time, and sending the exercise information to the terminal in real time, wherein the terminal is configured to determine, according to the exercise status, body parts trained by the user during the exercise; or acquiring a number of a movement performed by the user, generating in real time the exercise information including the exercise status and the number of the movement, and sending the exercise information to the terminal in real time, wherein the terminal is configured to compute a total energy consumption of the user based on the number of the movement and an energy consumption caused by a single movement.

15. A non-transitory computer-readable storage medium storing instructions that, when executed by a processor of a device, cause the device to perform:

determining critical force areas of a user on a mat;

determining exercise status of the user on the mat, according to variations of pressure values at the critical force areas, the pressure values being measured by pressure sensors at the critical force areas, wherein the exercise status of the user comprises a type of physical exercise taken by the user; and sending exercise information to a terminal, the exercise information including the exercise status, wherein the determining exercise status of the user on the mat is performed by:

periodically measuring, through the pressure sensors, the pressure values at the critical force areas;

determining a variation pattern of the pressure values at the critical force areas; and determining, according to a predefined corresponding relationship between exercise statuses and variation patterns of the pressure values, the exercise status corresponding to the variation pattern of the pressure values.

* * * * *